United States Patent [19]

Müllner et al.

[11] Patent Number: 5,519,164

[45] Date of Patent: May 21, 1996

[54] EXPRESSION OF A MULTIGENE RNA HAVING SELF-SPLICING ACTIVITY

[75] Inventors: Hubert Müllner; Rudolf Schneider, both of Kelkheim/Taunus; Eugen Uhlmann, Glashütten, all of Germany

[73] Assignee: Hoechst Aktiengesellschaft, Frankfurt, Germany

[21] Appl. No.: 326,812

[22] Filed: Oct. 20, 1994

Related U.S. Application Data

[63] Continuation of Ser. No. 143,375, Oct. 26, 1993, abandoned, which is a continuation of Ser. No. 910,263, filed as PCT/EP91/00145, Jan. 25, 1991, abandoned.

[30] Foreign Application Priority Data

Feb. 1, 1990 [DE] Germany .................. 40 02 885.2

[51] Int. Cl.$^6$ ............... A01H 5/00; C12N 15/52; C12N 15/64; C12N 15/67
[52] U.S. Cl. ............... 800/205; 536/23.1; 536/23.2; 435/91.31; 435/172.3; 435/240.4; 435/253.2; 435/320.1
[58] Field of Search ............... 536/23.2, 23.1; 435/240.4, 253.2, 320.1, 172.3, 91.31; 800/205

[56] References Cited

U.S. PATENT DOCUMENTS 5,168,053 12/1992 Altman et al. ............... 435/91

FOREIGN PATENT DOCUMENTS 0321201 6/1989 European Pat. Off.

OTHER PUBLICATIONS

Cech 1986 Scientific American 5:76–84.
Haseloff et al., Nature, vol. 334, Aug. 18, 1988, pp. 588–591.
Wohlleben et al., Elsevier Science Publishers, 1988, pp. 25–37.
Olke C. Uhlenbeck, Nature, vol. 328, Aug. 13, 1987, pp. 596–600.
Forster et al., Cell, vol. 49, Apr. 24, 1987, pp. 211–220.
Pietrzak et al., Nucleic Acid Research, vol. 14, No. 14, 1986, pp. 5857–5868.
Zaug et al., Nature, vol. 301, Feb. 17, 1983, pp. 578–583.
Hutchins et al., Nucleic Acid Research, vol. 14, No. 9, 1986, pp. 3627–3640.
Prody et al., Science 231, Mar. 28, 1986, pp. 1577–1580.
Alton et al., Nature, vol. 282, Dec. 1979, pp. 864–869.
Fromm et al., Proc. Natl. Acad. Sci. USA, vol. 82, Sep. 1985, pp. 5824–5828.
EMBO Journal, vol. 4, No. 2, 1985, pp. 277–284 An et al.
EMBO Journal, vol. 2, No. 12, 1983, pp. 2143–2150 Zambryski et al.
Olszewski et al., Nucleic Acid Research, vol. 16, No. 22, 1988, pp. 10765–10782.
Simon et al., Bio/Technology, Nov. 1983, pp. 784–791.
Shahin et al., Theoretical and Applied Genetics, 1986, pp. 720–777.
Masson et al., Plant Science, 53, 1987, pp. 167–176.
Zhan et al., Plant Molecular Biology, 1988, pp. 551–559.
McGranahan et al., Bio/Technology, vol. 6, Jul. 1988, pp. 800–804.
Novak et al., Bio/Technology, vol. 7, Feb. 1989, pp. 154–159.
Dzianott et al 1989 (Jul.) Proc. Natl. Acad. Sci. USA 86:4823–4827.
Tiara et al 1991 Nucleic Acids Research 19(19):5125–5130.
Chen et al 1992 Nucleic Acids Research 20(17):4581–4589.
Weizsäcker et al 1992 Biochem Biophys Res. Comm. 189(2):743–748.
Okhawa et al 1993 Proc Natl Acad Sci USA 90:11302–11306.

Primary Examiner—Patricia R. Moody
Attorney, Agent, or Firm—Curtis, Morris & Safford

[57] ABSTRACT

Expression of a multigene RNA having self-splicing activity

An RNA is expressed which can release two or more active genes by means of inserted ribozyme structures. The expression can be carried out in plants or other organisms.

8 Claims, No Drawings

EXPRESSION OF A MULTIGENE RNA HAVING SELF-SPLICING ACTIVITY

This application is a continuation of application Ser. No. 08/143,375, filed Oct. 26, 1993, now abandoned which is a continuation of application Ser. No. 07/910,263, filed as PCT/EP91/00145, Jan. 25, 1991, which is now abandoned.

RNA molecules can, under suitable conditions, catalyze reactions on other RNA molecules or autocatalytically cleave off fragments from their own molecules without the participation of proteins. For example, an intron having 413 nucleotides is deleted autocatalytically at the 3' end of the 23s rRNA of Tetrahymena thermophila and transformed into a circular form. This takes place by means of a number of phosphoester transfer reactions with guanosine cofactors participating (Cech, T. R., Nature 30, 578–583 (1983)). Depending on the RNA substrate or the reaction conditions chosen, the intron can function as specific ribonuclease, terminal transferase, phosphotransferase or acid phosphatase. In this connection, an RNA molecule can carry out several conversions without being changed itself and has the characteristics of an enzyme in this respect. For this reason, the term ribozyme has been introduced for RNA molecules having these properties.

It was possible to show similar reactions without participation of proteins also for some viroid RNAs and satellite RNAs. For example for avocado sunblotch viroid (ASBV) (Hutchins, C. J. et al. Nucleic Acids Res. 14, 3627–3640 (1986)), satellite RNA of tobacco ringspot virus (sTobSV) (Prody, G. A. et al., Science 231, 1577–1580 (1986)) and satellite RNA of luzerne transient streak virus (sLTSV) (Forster A. C. et al., Cell 49, 211–220 (1987)), self-processing seems to be a reaction essential for multiplication. During the replication of these RNAs circular forms are presumably formed which, as templates, lead to the synthesis of RNAs which are overlong. These transcripts are cut to the right genome length by the self-catalyzed endonucleolytic reactions.

The structures of the RNAs, which these presumably take on for the reaction, have been described as hammerheads (Forster A. C. et al., Cell 49, 211–220 (1987)); Haseloff, J. et al., Nature 334, 585–591 (1988)).

The cleavage sites for these RNA enzymes are specific and must have certain structural prerequisites in order to allow processing.

Surprisingly, it has now been found that host cells of any desired organisms can be transformed using vectors which contain DNA coding for ribozyme RNA linked to functional genes, so that said RNA is expressed and subsequently spliced.

The invention thus relates to:
1. A hybrid gene comprising one or more copies of a gene sequence coding for ribozyme RNA and of one or various functional genes, the gene sequences being linked via a spacer which, on the RNA level, represents a substrate for the ribozyme.
2. Host cells containing the gene characterized in 1.

In the following, the invention is described in detail, in particular in its preferred embodiments. Furthermore, the invention is defined by the contents of the claims.

A functional gene is a DNA section in the genome, which codes for a polypeptide. The polypeptide can, on its own, be a functional protein, or function as sub-unit of an enzyme complex.

The gene according to the invention is constructed in such a way that, starting from a promoter, several genes, for example entire synthetic pathways for the production of e.g. amino acids, such as glycine, nucleotides, secondary metabolites such as antibiotics, cofactors of enzymes, hormones, such as thyroid hormone, can be expressed in plants or microorganisms. The intention of this is, on the one hand, to produce foreign substances in appropriate plants or microorganisms and, on the other hand, to increase the yield in plants or microorganisms which naturally synthesize these substances. Genes coding for appropriate polypeptides can be employed according to the invention by using control sequences.

It is furthermore possible to employ several copies of a gene for a particular functional protein, e.g. in order to increase the yield of a protein such as insulin or transaminase.

Furthermore, the expression of one or more selection markers using the system according to the invention is possible. For this purpose, for example, genes for the following proteins can be employed: β-lactamase, β-galactosidase, phosphinotricine acetyltransferase, chloramphenicol acetyltransferase or thymidine kinase.

The acetyltransferase gene for the herbicide phosphinotricine and the Cat gene from the transposon Tn9 for the chloramphenicol acetyltransferase are preferably used.

The acetyltransferase gene from Streptomyces viridochromogenes (Wohleben, W. et al., Gene 70, 25–37 (1988)), can be assembled from synthetically prepared oligonucleotides, there also being the possibility of modifying it for the expression in plants. The gene gives resistance to phosphinotricine to transgenic plants which express the product constitutively. The Cat gene effects resistance to chloramphenicol. Like the acetyltransferase gene, the Cat gene acetylates its product. The Cat gene is derived from Tn9 (Alton, N. K. et al., Nature 15 282, 864–866, 1979) but is also commercially available.

The genes are linked by ribozyme substrate sequences, so-called spacers, and are released by a ribozyme structure domain of the same molecule. In this way, at least 2 and up to about 25 or more gene sequences can be expressed in one organism. The release can also take place via a separately expressed ribozyme molecule.

The appropriately transcribed RNA is essentially composed so that the ribozymes are preferably at the 3' or 5' end of the RNA molecule. A sequence of 40–50 nucleotides, which is entirely or in a partial region comprising at least 10, preferably 15–35, nucleotides complementary to the sequence of the ribozyme, is inserted as spacer. The ribozyme sequence of the RNA can, in this way, associate itself with the spacer and cut the latter immediately downstream of a defined sequence. A GUC triplet is preferably used as ribozyme cleavage site. The number of linked genes can, in each case, be multiplied by introducing further spacers, it being possible for the sequence of the latter to be the same or different from the first spacer introduced. If it is different, a further ribozyme structure domain matching this sequence is created in the same RNA molecule.

The spacer and ribozyme sequences necessary for this RNA can be prepared synthetically. The linkage to the genes is carried out by means of suitable linkers which have been synthesized on.

Spacers and ribozyme are synthesized to be analogous to ribozyme structures in nature (Uhlenbeck, O. C., Nature 328, 596–600, (1987). In this connection, these sequences can mimic naturally occurring ribozymes (Forster A. C. et al., Cell 49, 211–220, (1987)) or be constructed in such a way that the essential structures of the ribozyme are present, but that other sequences are chosen for nonessential parts. In the basic construction, the procedure by Haseloff, J. et al., Nature 334, 585–591, 1988 can essentially be carried out. A GUC sequence around which sequences which are complementary to a described ribozyme sequence are located in the direction of 5' and 3' is incorporated into the spacer part of the RNA.

Spacer and ribozyme on the RNA level can diagrammatically be described as follows:

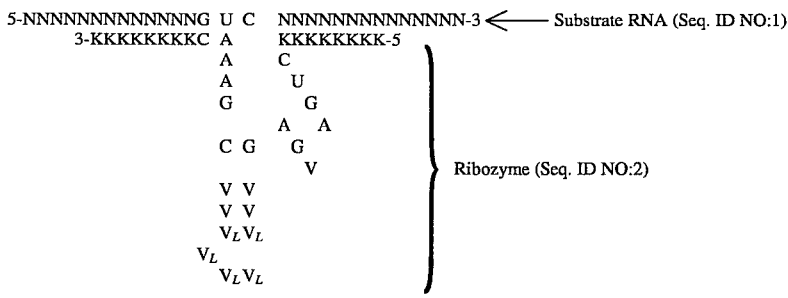

where
N are nucleotides of the substrate RNA, A, C, G or U
K are nucleotides complementary to N in the ribozyme
V are variable nucleotides A, C, G or U in the ribozyme and
$V_L$ are variable nucleotides A, C, G or U in the loop of the ribozyme.

The number of nucleotides of $V_L$ can be 0–550.

The gene according to the invention is cloned into an intermediary vector having a plant promoter. Vectors of this type are for example the plasmids pNCN (Fromm M. et al., PNAS 82., 5824–5826 (1985) or pNOS (An G. et al. EMBO J. 4, 277-276 (1985), or preferably pDH51 (Pietrzak, M. et al. NAR 14, 5857–5861, (1986).

After subsequent transformation of *E. coli*, such as e.g. *E. coli* MC 1061, DH1, DK1, GM48 or XL-1, positive clones are identified by methods known per se (Maniatis et al., Lab. Manual), such as plasmid minipreparation and cleavage using an appropriate restriction enzyme. These positive clones are then subcloned in a binary plant vector. pGV3850 (Zambrysky, P. et al., EMBO J. 2, 2143-2150 (1983)) or pOCA18 (Olszewski, N., NAR 16, 10765–10782, (1988)) can be employed as plant vectors. Advantageously pOCA18 is used.

The binary plant vectors obtained which contain in the T-DNA a plant promoter with the attached DNA fragment which is constructed as specified above are used to transform plants. This can be carried out by techniques such as electroporation or microinjection.

Preferably, the cocultivation of protoplasts or the transformation of pieces of leaf by agrobacteria is used. For this purpose, the plant vector construct is transferred by transformation with purified DNA or, mediated by a helper strain such as *E. coli* SM10 (Simon R. et al., Biotechnology 1, 784–791 (1983)), in Agrobakterium tumefaciens such as A 282 via triparental mating using a Ti plasmid. Direct transformation and triparental mating were carried out as described in, "Plant Molecular Biology Manual" (Kluwer Academic Publishers, Dardrecht (1988)).

Basically all plants can be transformed using the binary plant vectors according to the invention and carrying constructed DNA. Dicotyledonous plants, in particular useful plants, which produce or store for example starch, carbohydrates, proteins or fats in usable amounts in their organs, or produce fruit and vegetables, or provide spices, fibers and technically usable products or medicaments, dyes or waxes, as well as fodder plants are preferred. Examples which may be mentioned are tomato, strawberry, avocado, and plants which carry tropical fruit, e.g. papaya, mango, but also pear, apple, nectarine, apricot or peach. Furthermore, as examples of plants to be transformed all types of cereal, rape, potatoes, soya bean, cotton, corn, sugar beet or sunflower may be listed.

The transformed cells are selected with the aid of a selection medium, grown to give a callus and regenerated to the plant on an appropriate medium (Shain et al., Theor. appl. Genet.72, 770–770 (1986); Masson, J. et al., Plant Science 53, 167–176 (1987); Zhan et al., Plant Mol. Biol. 11, 551–559 (1988); McGranaham et al., Bio/Technology 6, 800–804 (1988); Novrate et al., Bio/Technology 7, 154–159 (1989).

The resulting plant is altered by the transformation insofar as the RNA which is expressed with the aid of the constructed oligonucleotides is cleaved open in the cells at GUC cleavage sites by the ribozyme activity in order to release the genes.

It is also possible to use the described system in bacteria, cell cultures, yeasts or other eukaryotic organisms.

The examples which follow illustrate the invention in more detail.

EXAMPLES

1) DNA structures used
a) Acetyltransferase gene having SalI linkers (SEQ ID NOS.: 3 and 4, respectively)

```
              9        18        27        36        45
5' GTC  GAC  ATG  TCT  CCG  GAG  AGG  AGA  CCA  GTT  GAG  ATT  AGG  CCA  GCT
3'           G    TAC  AGA  GGC  CTC  TCC  TCT  GGT  CAA  CTC  TAA  TCC  GGT  CGA 54        63        72        81        90
    ACA  GCA  GCT  GAT  ATG  GCC  GCG  GTT  TGT  GAT  ATC  GTT  AAC  CAT  TAC
    TGT  CGT  CGA  CTA  TAC  CGG  CGC  CAA  ACA  CTA  TAG  CAA  TTG  GTA  ATG 99        108       117       126       135
    ATT  GAG  ACG  TCT  ACA  GTG  AAC  TTT  AGG  ACA  GAG  CCA  CAA  ACA  CCA
    TAA  CTC  TGC  AGA  TGT  CAC  TTG  AAA  TCC  TGT  CTC  GGT  GTT  TGT  GGT
```

-continued

```
         144         153         162         171         180
CAA GAG TGG ATT GAT GAT CTA GAG AGG TTG CAA GAT AGA TAC CCT
GTT CTC ACC TAA CTA CTA GAT CTC TCC AAC GTT CTA TCT ATG GGA 189         198         207         216         225
TGG TTG GTT GCT GAG GTT GAG GGT GTT GTG GCT GGT ATT GCT TAC
ACC AAC CAA CGA CTC CAA CTC CCA CAA CAC CGA CCA TAA CGA ATG 234         243         252         261         270
GCT GGG CCC TGG AAG GCT AGG AAC GCT TAC GAT TGG ACA GTT GAG
CGA CCC GGG ACC TTC CGA TCC TTG CGA ATG CTA ACC TGT CAA CTC 279         288         297         306         315
AGT ACT GTT TAC GTG TCA CAT AGG CAT CAA AGG TTG GGC CTA GGA
TCA TGA CAA ATG CAC AGT GTA TCC GTA GTT TCC AAC CCG GAT CCT 324         333         342         351         360
TCC ACA TTG TAC ACA CAT TTG CTT AAG TCT ATG GAG GCG CAA GGT
AGG TGT AAC ATG TGT GTA AAC GAA TTC AGA TAC CTC CGC GTT CCA 369         378         387         396         405
TTT AAG TCT GTG GTT GCT GTT ATA GGC CTT CCA AAC GAT CCA TCT
AAA TTC AGA CAC CAA CGA CAA TAT CCG GAA GGT TTG CTA GGT AGA 414         423         432         441         450
GTT AGG TTG CAT GAG GCT TTG GGA TAC ACA GCC CGG GGT ACA TTG
CAA TCC AAC GTA CTC CGA AAC CCT ATG TGT CGG GCC CCA TGT AAC 459         468         477         486         495
CGC GCA GCT GGA TAC AAG CAT GGT GGA TGG CAT GAT GTT GGT TTT
GCG CGT CGA CCT ATG TTC GTA CCA CCT ACC GTA CTA CAA CCA AAA 504         513         522         531         540
TGG CAA AGG GAT TTT GAG TTG CCA GCT CCT CCA AGG CCA GTT AGG
ACC GTT TCC CTA AAA CTC AAC GGT CGA GGA GGT TCC GGT CAA TCC 549         558
CCA GTT ACC CAG ATC TGA G.          3'
GGT CAA TGG GTC TAG ACT CAG CTG     5'
``` b) Spacer having SalI and HindIII linkers (SEQ ID NOS.: 5 and 6, respectively)

```
         9          18         27         36
5' TCG ACT TAC GGC TAA AAT GGT CAG TAT CCC CAA AAG GCG GCC GC  3'
3'         GA ATG CCG ATT TTA CCA GTC ATA GGG GTT TTC CGC CGG CGT CGA  5'
``` c) Cat gene from Tn9 according to Alton et al. Nature 282, 864–866 (1979)

d) Ribozyme structure domain having HindIII and PstI linkers (SEQ ID NOS.: 7 and 8, respectively)

```
         9          18         27         36         45
5' AGC TGC GGC CGC TTA CGG CTA AAA TGG TCA GTA TCC CCA AAG GGG
3'     CG CCG GCG AAT GCC GAT TTT ACC AGT CAT AGG GGG TTT CCC 54         63         72         81         90
GTA CCC CTT TCG GGC ATA CTC TGA TGA GTC CGT GAG GAC GAA ACC
CAT GGG GAA AGC CCG TAT GAG ACT ACT CAG GCA CTC CTG CTT TGG 99         108
ATT TTA GCC GTA ACT GCA  3'
TAA AAT CGG CAT TG       5'
```

The oligonucleotides under a), b) and d) were synthesized by means of a DNA synthesizer by the phosphoramidite method.

2) Cloning the fragments

The DNA specified under 1a)–d) was ligated in equal molar amounts and incorporated into the SalI/PstI sites of the vector pDH51. Positive clones were identified by hybridization with all 4 radioactively labeled DNA sections used.

3) Cloning into pOCA18

The plasmid pOCA18 is reproducibly described in Olszewski, N. et al. NAR 16, 10765–10782 (1988).

An NosI/HindIII fragment with a length of 2.4 kbp was isolated from the described vector pDH51 with the inserted construction and, after filling in the ends, cloned into a pOCA18 vector which had been cut using Bam HI and filled in. Positive clones were detected by hybridization with $^{32}$P-labeled DNA.

4) Transformation of agrobacteria

The pOCA18 vector with the described 35S promoter/insert was transferred into the agrobacteria strain A 282 (Pharmacia Freiburg, FR Germany, or ATCC 37349, USA). This was carried out by triparental mating with the aid of the E. coli strain SM10 (Simon, R. et al. Bio/Technology 1, 784–791, 1983). For this purpose, equal amounts of the bacteria were applied together onto a filter overnight, rinsing with 2 ml of 10 mM $MgSO_4$ was carried out and aliquots thereof were applied to YEB plates containing tetracycline and rifampicin (YEB: 1% yeast extract, 1% peptone, 0.5% NaCl). It was possible to detect positive agrobacteria by hybridization.

5) Transformation of tobacco

The agrobacteria were grown in YEB medium (1% yeast extract, 1% peptone, 0.5% NaCl) containing tetracycline and rifampicin. 20 ml of the bacteria were spun down, washed once in YEB medium and suspended in 20 ml of 10 mM $MgSO_4$ in a Petri dish. The plant material used was Nicotiana tabacum Wisconsin 38. The plants had been cultivated for 4 weeks under sterile conditions on 2MS medium Murashige T. et al., Physiol. Plant 15, 473–497 (1962) at 25° C. with 16 hours of light per day. A 1 $cm^2$ leaf piece was cut off from these plants, wounded using sterile emery paper and immersed in the bacteria culture for 30 sec. The leaf pieces were maintained on MS medium, as described above for 2MS, at 25° C. for 2 days and were then washed with liquid 2MS medium. The leaf pieces were then transferred onto MSC 10 plates (as MS containing 1.5% agar) containing 100 µg/ml of kanamycin. After 56 weeks, it was possible to replant regenerated plants into larger vessels where they formed roots after 23 weeks.

6) Detection of transformation

DNA was isolated from transformed tobacco plants with an age of about 8 weeks using standard methods (Maniatis et al., Lab. Journal), transferred to nitrocellulose membranes and hybridized with a $^{32}P$-labeled insert DNA.

It was possible to demonstrate an incorporation of the desired sequences in the DNA of the plant.

7) Detection of the expression of the RNA

RNA was isolated from the abovementioned tobacco plants from a second leaf sample, was transferred from a formaldehyde gel to nitrocellulose and hybridized as above. It was possible to detect several bands which showed the expected sizes.

8) Detection of in vitro function of the ribozyme RNA

The multifunctional RNA was produced from the pBluescript SK+ clones containing the inserted entire oligo using T3 or T7 polymerase in a reaction mixture (Stratagene, Product Information for SK+) and was then isolated. Hybridization of this RNA with individual components showed that the RNA was cleaved open.

9) Detection of in vivo activity of the genes

Transformed plants showed growth on 2MS medium containing phosphinotricine. In a spray experiment, the plants likewise proved to be resistant. An experiment in order to acetylate chloramphenicol showed that the plants express an active enzyme.

---

We claim:

1. A hybrid gene comprising in a 5' to 3' direction of transcription, a promoter functional in plants, a first DNA coding sequence and at least one other DNA coding sequence separated by a spacer DNA sequence and operably joined at either the 3' or 5' end to a ribozyme which is specific to the spacer but not to any of the coding sequences, so that intact mRNA for each of the coding sequences can be cleaved from the hybrid gene mRNA by the ribozyme acting at the RNA substrate site formed by each spacer, and wherein the coding sequences each have control sequences so that each coding sequence can be translated.

2. A hybrid gene as claimed in claim 1, wherein the first DNA coding sequence codes for phosphinothricin acetyltransferase and the at least one other DNA coding sequence codes for chloramphenicol acetyltransferase.

3. A vector comprising a gene as claimed in claim 1 or 2.

4. A bacterial cell comprising the gene of claims 1 or 2.

5. A plant cell comprising the gene of claims 1 or 2.

6. Plant tissue comprising the cell of claim 7.

7. A plant comprising the gene of claims 1 or 2.

8. A method for making a plant which expresses two or more DNA coding sequences comprising: (1) transforming a plant cell with a hybrid gene comprising in a 5' to 3' direction of transcription: a promoter functional in plants, a first DNA coding sequence and at least one other DNA coding sequence separated by a spacer DNA sequence and operably joined at either the 3' or 5' end to a ribozyme which is specific to the spacer but not to any of the coding sequences so that intact mRNA for each of the coding sequences can be cleaved from the hybrid gene mRNA by the ribozyme acting at the RNA substrate site formed by each spacer, and wherein the coding sequences each have control sequences so that each coding sequence can be translated; and (2) regenerating from the cell a whole plant having cells wherein mRNA for each of the coding sequences is separated by cleavage of the hybrid gene mRNA at each spacer and the cells detectably express products of the coding sequences of the hybrid gene.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( A ) NAME/KEY: misc_RNA
        ( B ) LOCATION: 1..13
        ( D ) OTHER INFORMATION: "N represents nucleotides of the substrate RNA, A,C,G or U."

( i x ) FEATURE:
        ( A ) NAME/KEY: misc_RNA
        ( B ) LOCATION: 17..30
        ( D ) OTHER INFORMATION: "N is representing nucleotides of the substrate RNA, A,C,G or U."

( x i ) SEQUENCE DESCRIPTION: SEQ ID NO:1:

NNNNNNNNN NNNGUCNNNN NNNNNNNNNN  30

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear (ix) FEATURE:
  (A) NAME/KEY: misc_RNA
  (B) LOCATION: 1..8
  (D) OTHER INFORMATION: "N (which are the variable K's in the diagram on page 5 of the application) represents nucleotides complementary to N in the ribozyme."

(ix) FEATURE:
  (A) NAME/KEY: misc_RNA
  (B) LOCATION: 13..26
  (D) OTHER INFORMATION: "Positions 13,17,18,25, and 26 are represented by V's in the diagram on page 5 of the application. They are defined as variable nucleotides A,C,G or U in the ribozyme."

(ix) FEATURE:
  (A) NAME/KEY: misc_RNA
  (B) LOCATION: 19..24
  (D) OTHER INFORMATION: "Positions 19-24 represented by VL on the diagram on page 5 of the application are variable nucleotides A,C,G or U in the loop of the ribozyme. The number of nucleotides of VL can be 0- 550."

(xi) SEQUENCE DESCRIPTION: SEQ ID NO:2:

| | | | | |
|---|---|---|---|---|
| NNNNNNNCU | GANGAGNNNN | NNNNNCGAA | ACNNNNNNN | 40 |

(2) INFORMATION FOR SEQ ID NO:3:

(i) SEQUENCE CHARACTERISTICS:
    (A) LENGTH: 559 base pairs
    (B) TYPE: nucleic acid
    (C) STRANDEDNESS: single
    (D) TOPOLOGY: linear (xi) SEQUENCE DESCRIPTION: SEQ ID NO:3:

| | | | | | | |
|---|---|---|---|---|---|---|
| GTCGACATGT | CTCCGGAGAG | GAGACCAGTT | GAGATTAGGC | CAGCTACAGC | AGCTGATATG | 60 |
| GCCGCGGTTT | GTGATATCGT | TAACCATTAC | ATTGAGACGT | CTACAGTGAA | CTTTAGGACA | 120 |
| GAGCCACAAA | CACCACAAGA | GTGGATTGAT | GATCTAGAGA | GGTTGCAAGA | TAGATACCCT | 180 |
| TGGTTGGTTG | CTGAGGTTGA | GGGTGTTGTG | GCTGGTATTG | CTTACGCTGG | GCCCTGGAAG | 240 |
| GCTAGGAACG | CTTACGATTG | GACAGTTGAG | AGTACTGTTT | ACGTGTCACA | TAGGCATCAA | 300 |
| AGGTTGGGCC | TAGGATCCAC | ATTGTACACA | CATTTGCTTA | AGTCTATGGA | GGCGCAAGGT | 360 |
| TTTAAGTCTG | TGGTTGCTGT | TATAGGCCTT | CCAAACGATC | CATCTGTTAG | GTTGCATGAG | 420 |
| GCTTTGGGAT | ACACAGCCCG | GGGTACATTG | CGCGCAGCTG | GATACAAGCA | TGGTGGATGG | 480 |
| CATGATGTTG | GTTTTTGGCA | AAGGGATTTT | GAGTTGCCAG | CTCCTCCAAG | GCCAGTTAGG | 540 |
| CCAGTTACCC | AGATCTGAG | | | | | 559 |

(2) INFORMATION FOR SEQ ID NO:4:

(i) SEQUENCE CHARACTERISTICS:
    (A) LENGTH: 559 base pairs
    (B) TYPE: nucleic acid
    (C) STRANDEDNESS: single
    (D) TOPOLOGY: linear (xi) SEQUENCE DESCRIPTION: SEQ ID NO:4:

| | | | | | | |
|---|---|---|---|---|---|---|
| GTCGACTCAG | ATCTGGGTAA | CTGGCCTAAC | TGGCCTTGGA | GGAGCTGGCA | ACTCAAAATC | 60 |
| CCTTTGCCAA | AAACCAACAT | CATGCCATCC | ACCATGCTTG | TATCCAGCTG | CGCGCAATGT | 120 |
| ACCCCGGGCT | GTGTATCCCA | AAGCCTCATG | CAACCTAACA | GATGGATCGT | TTGGAAGGCC | 180 |
| TATAACAGCA | ACCACAGACT | TAAAACCTTG | CGCCTCCATA | GACTTAAGCA | AATGTGTGTA | 240 |
| CAATGTGGAT | CCTAGGCCCA | ACCTTTGATG | CCTATGTGAC | ACGTAAACAG | TACTCTCAAC | 300 |

| | | | | | | |
|---|---|---|---|---|---|---|
|TGTCCAATCG|TAAGCGTTCC|TAGCCTTCCA|GGGCCCAGCG|TAAGCAATAC|CAGCCACAAC|360|
|ACCCTCAACC|TCAGCAACCA|ACCAAGGGTA|TCTATCTTGC|AACCTCTCTA|GATCATCAAT|420|
|CCACTCTTGT|GGTGTTTGTG|GCTCTGTCCT|AAAGTTCACT|GTAGACGTCT|CAATGTAATG|480|
|GTTAACGATA|TCACAAACCG|CGGCCATATC|AGCTGCTGTA|GCTGGCCTAA|TCTCAACTGG|540|
|TCTCCTCTCC|GGAGACATG| | | | |559|

( 2 ) INFORMATION FOR SEQ ID NO:5:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | |
|---|---|---|---|---|
|TCGACTTACG|GCTAAAATGG|TCAGTATCCC|CCAAAGGCGG|CCGC|44|

( 2 ) INFORMATION FOR SEQ ID NO:6:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | |
|---|---|---|---|---|
|AGCTGCGGCC|GCCTTTGGGG|GATACTGACC|ATTTTAGCCG|TAAG|44|

( 2 ) INFORMATION FOR SEQ ID NO:7:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
|AGCTGCGGCC|GCTTACGGCT|AAAATGGTCA|GTATCCCCCA|AAGGGGTACC|CCTTTCGGGC|60|
|ATACTCTGAT|GAGTCCGTGA|GGACGAAACC|ATTTTAGCCG|TAACTGCA| |108|

( 2 ) INFORMATION FOR SEQ ID NO:8:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | |
|---|---|---|---|---|---|
|GTTACGGCTA|AAATGGTTTC|GTCCTCACGG|ACTCATCAGA|GTATGCCCGA|AAGGGGTACC|60|
|CCTTTGGGGG|ATACTGACCA|TTTTAGCCGT|AAGCGGCCGC| | |100|